United States Patent
Combeau et al.

(10) Patent No.: US 6,930,124 B2
(45) Date of Patent: Aug. 16, 2005

(54) COMPOUNDS DERIVED FROM OXINDOLES AND THEIR THERAPEUTIC APPLICATION IN CANCER TREATMENT

(75) Inventors: Cécile Combeau, Fontenay aux Roses (FR); Patrick Mailliet, Fontenay sous Bois (FR); Marielle Chiron, Paris (FR)

(73) Assignee: Aventis Pharma S. A., Antony (FR)

( * ) Notice: Subject to any disclaimer, the term of this patent is extended or adjusted under 35 U.S.C. 154(b) by 0 days.

(21) Appl. No.: 10/659,094

(22) Filed: Sep. 10, 2003

(65) Prior Publication Data

US 2004/0082645 A1 Apr. 29, 2004

Related U.S. Application Data

(63) Continuation of application No. PCT/FR02/00852, filed on Mar. 11, 2002.

(30) Foreign Application Priority Data

Mar. 13, 2001 (FR) .............................. 01 03408

(51) Int. Cl.⁷ ................. A61K 31/4015; A61K 31/404; C07D 209/04
(52) U.S. Cl. ................ 514/414; 514/418; 548/468; 548/486
(58) Field of Search ............................ 514/414, 418, 514/186; 548/468, 486, 469, 416

(56) References Cited

U.S. PATENT DOCUMENTS

| | | | | |
|---|---|---|---|---|
| 5,792,783 A | * | 8/1998 | Tang et al. | 514/397 |
| 5,834,504 A | * | 11/1998 | Tang et al. | 514/418 |
| 5,880,141 A | * | 3/1999 | Tang et al. | 514/339 |
| 5,883,113 A | * | 3/1999 | Tang et al. | 514/418 |
| 5,883,116 A | * | 3/1999 | Tang et al. | 514/418 |
| 5,886,020 A | * | 3/1999 | Tang et al. | 514/418 |
| 6,051,593 A | * | 4/2000 | Tang et al. | 514/397 |
| 6,133,305 A | * | 10/2000 | Tang et al. | 514/418 |
| 6,225,335 B1 | * | 5/2001 | Tang et al. | 514/418 |
| 6,313,158 B1 | * | 11/2001 | Tang et al. | 514/414 |
| 6,316,635 B1 | * | 11/2001 | Tang et al. | 548/312.1 |
| 6,506,763 B2 | * | 1/2003 | Tang et al. | 514/274 |
| 6,579,897 B2 | * | 6/2003 | Tang et al. | 514/414 |
| 6,696,448 B2 | * | 2/2004 | Tang et al. | 514/254.09 |
| 6,696,463 B2 | * | 2/2004 | Tang et al. | 514/300 |
| 6,846,839 B1 | * | 1/2005 | Tang et al. | 514/397 |

FOREIGN PATENT DOCUMENTS

| | | |
|---|---|---|
| WO | WO 96/40116 | 12/1996 |
| WO | WO 00/35908 | 6/2000 |

* cited by examiner

Primary Examiner—Joseph K. McKane
Assistant Examiner—Susannah E. Lee
(74) Attorney, Agent, or Firm—Joseph Strupczewski

(57) ABSTRACT

The invention relates to compounds of formula (I)

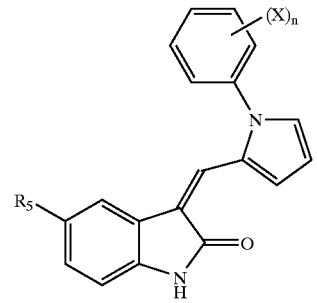

in which $R_5$ is chosen from the group consisting of:

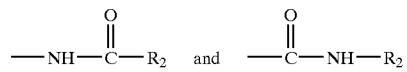

in which $R_2$ is a $C_1$–$C_3$ alkyl group
in which X may be Cl, Br, or F
in which n is between 1 and 3, in the E or Z form, or a mixture of the two isomeric forms, possessing antimitotic, antiproliferative and antivascular properties through inhibition of the polymerization of tubulin into microtubules

10 Claims, No Drawings

COMPOUNDS DERIVED FROM OXINDOLES AND THEIR THERAPEUTIC APPLICATION IN CANCER TREATMENT

This application is a continuation of International Application No. PCT/FR02/00852 filed Mar. 11, 2002, which claims the benefit of priority of French Application No.01/03408 filed Mar. 13, 2001

The present invention relates to compounds derived from oxindoles, their use for inhibiting the vascularization of a tumour mass and/or their therapeutic application for the preparation of a medicament having an antivascular pharmacological property.

The main stages of the cell cycle of a eukaryote are as follows:

After the M phase, which consists of nuclear division (mitosis) and cytoplasmic division (cytodieresis), the daughter cells begin the interphase of a new cycle. This interphase begins with the G1 phase, during which an increased resumption of the biosynthetic activities of the cell is observed. The S phase begins when the synthesis of DNA commences and ends when the chromosomes have replicated (each chromosome is then composed of two identical sister chromatids). The cell then enters the G2 phase (last phase of the interphase), which continues until the beginning of mitosis, initiating the M phase. Cell division thus comprises the division of the chromosomes (or mitosis) and the division of the cytoplasm (or cytodieresis).

The process of mitosis comprises several phases:
- the prophase, characterized by condensation of the DNA and duplication in the as yet intact nucleus of the chromosomes into two chromatids joined by a centromere,
- the metaphase, where the dissolution of the nuclear membrane and the formation of a bundle of microtubules and proteins, the mitotic spindle, on which the chromosomes are placed in an equatorial position to form the metaphase plate, are observed,
- the anaphase, which consists in the separation and the migration of the chromatids on either side of the nucleus towards the poles of the mitotic spindle by attaching to the microtubules with the aid of a structure called kinetochore,
- the telophase: during this stage, the chromosomes recover the shape of two networks of diffuse fine chromatin, the nuclear envelope forms again, and then the cytoplasmic membrane, and a new network of microtubules appears in the cytoplasm.

The microtubules are microscopic fibres which form part of the cellular cytoskeleton and play a crucial role in the division, transport and mobility of the cell. The microtubules are composed of tubulin, a heterodimeric protein which polymerizes to reversibly form the microtubules which themselves assemble to compose the mitotic spindle during the metaphase.

By virtue of its formation in the cell, tubulin thus represents a target of choice for antimitotic compounds for antitumour use.

It is now well established that the development of an intra- or peritumoral vascularization is a key event both for the growth of a tumour and for metastatic dissemination through the blood. A blood vessel indeed feeds millions of cells. Thus, it is vital in an anticancer approach to limit the blood supply to the site of the tumour. Angiogenesis is a neovascularization mechanism which is created from an existing capillary network. It is possible either to prevent the formation of new blood vessels in the tumour (antiangiogenesis) or to envisage a destruction of the existing vessels with the aim of limiting the supply of nutrients to the tumour (antivascular approach).

In the antiangiogenic approach, which is a cytostatic approach, the angiogenic factors generally synthesized by the tumours, such as VEGF (Vascular Endothelial Growth Factor), PD-ECGF (Platelet Derived Endothelial Cell Growth Factor) or b-FGF (basic Fibroblast Growth Factor), are blocked. The growth of new vessels can also be inhibited with antiangiogenic molecules such as the inhibitors of the receptor tyrosine kinase KDR, anti-integrin antibodies, or by natural antiangiogenic polypeptides such as angiostatin or endostatin.

By contrast, the antivascular approach induces cytotoxic effects. Colchicine, colcemide, and nocadazole inhibit the polymerization of tubulin. Vinblastine and vincristine, in low concentrations, also inhibit the polymerization, but by interacting at a site distinct from the preceding one, at a higher concentration, the latter two molecules can cause aggregation of tubulin. Taxol, by contrast, stimulates the assembly of tubulin into microtubules and stabilizes the preformed microtubules.

All these compounds, whether they polymerize tubulin or depolymerize the microtubules, nevertheless have the same antimitotic and therefore cytotoxic effect on endothelial and tumour cells. Some compounds inhibiting the polymerization of the microtubules, such as colchicine, vincristine or vinblastine, have furthermore been characterized for their antivascular activity, that is to say that they induce within a few hours an arrest of blood flow in the tumour and haemorrhagic necrosis in experimental models of tumour.

Many of these compounds which are capable of binding to tubulin, such as combrestatin A4 or analogues of taxol, are insoluble in water. Patent Application WO00/48606 describes a method which, by virtue of a phosphorylation, allows the solubilization of combretastatin A4 in water. This phosphorylated compound is in the form of a prodrug (that is to say inactive) but is capable of becoming active in vivo under the action of nonspecific phosphatases and thus of stopping the cell cycle in the G2/M phase.

patent application WO96/40116 describes oxindole derivatives for modulating the signal for transducing protein tyrosine kinase (PTK).

The Applicant has discovered a family of chemical compounds derived from oxindoles or indolin-2-ones having an inhibitory action on the polymerization of tubulin, a cytotoxic effect on tumour epithelial cells and an action on cell detachment. The expression "cell detachment" is understood to mean the detachment of the endothelial cells of the vessels which will cause disorganisation of these vessels and, consequently, a stasis of blood flow and subsequent necrosis of the tumour through a nonsupply essentially of growth factors and of oxygen.

The subject of the invention is the use of compounds derived from indolin-2-one for inhibiting the polymerization of tubulin, which has the consequence of interrupting the cell cycle in the G2/M phase. By virtue of the antimitotic and therefore cytotoxic action of the invention, these compounds can exert an antitumour effect. In addition, by virtue of their mechanism of action—inhibition of the polymerization of tubulin—they can exert an antivascular effect on the tumours.

The subject of the present invention is thus the compounds of formula (I)

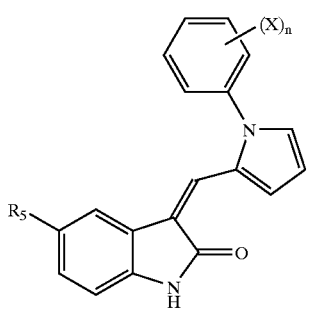

in which $R_5$ is chosen from the groups:

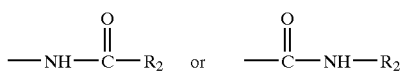

in which $R_2$ is a $C_1$–$C_3$ alkyl group
in which X may be Cl, Br, or F
in which n is between 1 and 3, in the E or Z form, or a mixture of the two isomeric forms.

In the compounds of formula (I), $R_2$ preferably denotes a methyl group, X is preferably chlorine, n is preferably equal to 2.

The subject of the present invention is most particularly the compounds of formula (I) as defined above, corresponding to the following formulae:

3-[N-(3,5-dichlorophenyl)pyrrol-2-yl]-5-acetylaminoindolin-2-one

3-[N-(3-chlorophenyl)pyrrol-2-yl]-5-acetylaminoindolin-2-one

The products of general formula (I), in which $R_5$, and X and n are as described above, can be obtained by coupling an indolin-2-one of general formula (II), in which $R_5$ is as described above, with an N-phenylpyrrole-2-carboxaldehyde of general formula (III), in which X and n are as described above, according to the scheme below:

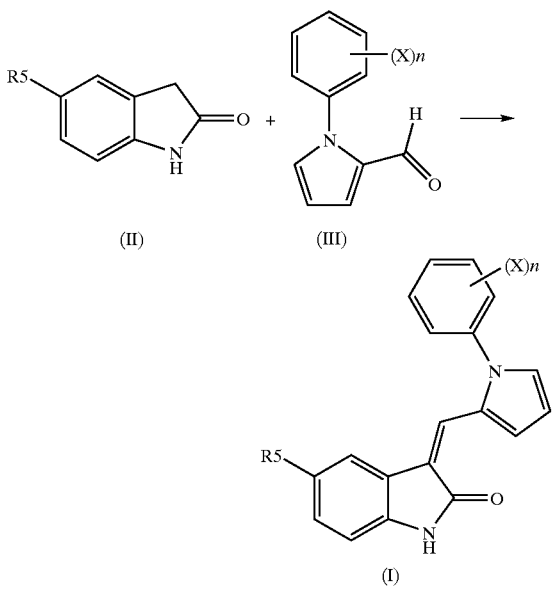

The coupling reaction is generally carried out under the conditions described by E. Knoevenagel (Chem. Ber. 1900, 23, 172), namely in a protic solvent such as methanol or ethanol, in the presence of a catalytic quantity of an organic base such as piperidine, at a temperature between 20° C. and the reflux temperature of the solvent used.

The indolin-2-ones of general formula (II) and the N-phenylpyrrole-2-carboxaldehydes of formula (III), in which $R_5$, X and n respectively are as described above, are either commercially available or prepared according to the conditions described in the literature.

The compounds of the present invention as defined above possess antimitotic properties through inhibition of the polymerization of tubulin into microtubules which are key components in the establishment of the mitotic spindle during cell division. Thus, molecules interfering with the polymerization of tubulin are capable of limiting inopportune cell proliferations such as those observed in cancers.

The compounds of the present invention possess, in addition to their inhibitory properties specific for tubulin, cellular effects such as antiproliferative and antivascular properties. The compounds of the present invention are in particular useful in the context of the therapy of primary tumours of cancers.

These properties justify their application in therapy and the subject of the invention is particularly, as medicaments, the products of formula (I) as defined above, in a pharmaceutically acceptable medium.

These pharmaceutical compositions may be administered orally, parenterally or locally by topical application to the skin and the mucous membranes or by intravenous or intramuscular injection. These compositions may be solids or liquids and may be provided in all the pharmaceutical forms commonly used in human medicine such as, for example, simple or coated tablets, pills, lozenges, gelatin capsules, drops, granules, preparations for injection, ointments, creams or gels. They are prepared according to the customary methods. The active ingredient may be incorporated therein in excipients normally used in these pharmaceutical compositions, such as talc, gum arabic, lactose, starch, magnesium stearate, cocoa butter, aqueous or non-aqueous vehicles, fatty substances of animal or plant origin, paraffin derivatives, glycols, various wetting, dispersing or emulsifying agents, preservatives.

The customary dosage, which can vary according to the product used and the subject treated, may be for example from 0.05 to 5 grams per day in adults.

The following examples illustrate the invention without, however, limiting it:

EXAMPLE 1

3-[N-(3,5-Dichlorophenyl)pyrrol-2-yl]-5-acetylaminoindolin-2-one 2.68 g (11 mmol) of 3-[N-(3,5-dichlorophenyl)pyrrole-2-carboxaldehyde are added to a solution of 2.12 g (11 mmol) of 5-acetylaminoindolin-2-one in 220 ml of ethanol containing 0.5 ml of piperidine. The reaction medium is heated under reflux for 3 hours. After cooling, the precipitate formed is drained, washed with twice 5 ml of ice-cold ethanol and dried under reduced pressure. 1.81 g (40%) of 3-[N-(3,5-dichlorophenyl)pyrrol-2-yl]-5-acetylaminoindolin-2-one are thus obtained in the form of a yellow solid whose characteristic is the following: melting point=267° C.

EXAMPLE 2

3-[N-(3-Chlorophenyl)pyrrol-2-yl]-5-acetylaminoindolin-2-one

By carrying out the procedure as in Example 1, but starting with 1.05 g (5 mmol) of 5-acetylaminoindolin-2-one in 150 ml of ethanol and 0.95 g (10 mmol) of 3-[N-(3-chlorophenyl)pyrrole-2-carboxaldehyde, 0.32 g (17%) of 3-[N-(3-chlorophenyl)pyrrol-2-yl]-5-acetylaminoindolin-2-one is obtained in the form of an orange solid whose characteristic is the following: melting point=251° C.

EXAMPLE 3

Parallel Synthesis of 3-(aryl)methyleneindolin-2-one of General Formula (I)

0.5 mmol of indolyl-2-one of general formula (II), 0.5 mmol of an aromatic aldehyde of general formula (III), 5 ml of ethanol and 1 drop of piperidine are introduced into a heating magnetic reactor with a Zymark STEM RS2050 type condenser containing 25 wells in parallel each provided with a glass tube of 50 ml. The reaction medium is heated under reflux overnight. After cooling, and diluting with 5 ml of water, the precipitate formed is drained and dried under reduced pressure. The 3-(aryl)methyleneindolin-2-ones of general formula (I) are thus obtained which can be represented, without limitation, by 3-[N-(3,5-dichlorophenyl)pyrrol-2-yl]indolin-2-one-5-yl-N-methylcarboxamide (Example 3–1).

EXAMPLE 4

Evaluation of the Inhibition of Polymerization of Tubulin

The tubulin is purified from pig brains (Shelanski et al., 1973, Proc. Natl. Acad. Sci. USA, 70, 765–768. Weingarten et al., 1975, Proc. Natl. Acad. Sci. USA, 72, 1858–1862). Briefly, the brains are ground and centrifuged in an extraction buffer. The tubulin present in the supernatant of the extract undergoes two successive cycles of polymerization at 37° C. and depolymerization at 4° C., before being separated from the MAPs (Microtubule Associated Proteins) by chromatography on a P11 phosphocellulose column (Whatman). The tubulin thus isolated is pure at more than 95%. It is stored in a buffer called RB/2 30% glycerol having the composition MES-NaOH [2-(N-morpholino) ethanesulfonic acid] 50 mM, pH 6.8; $MgCl_2$ 0.25 mM; EGTA 0.5 mM; glycerol 30% (v/v), GTP (guanosine-5'-triphosphate) 0.2 mM.

The polymerization of tubulin into microtubules is monitored by turbidimetry: the tubulin is adjusted to a concentration of 10 μM in RB/2 30% glycerol buffer to which 1 mM GTP and 6 mM $MgCl_2$ are added. The polymerization is initiated by increasing the temperature from 6° C. to 37° C. in a cuvette having an optical path length of 1 cm, placed in a UVIKON 931 spectrophotometer (Kontron) equipped with a thermostated cuvette holder. The increase in the turbidity of the solution is monitored at 350 nm.

The test products are dissolved at 10 mM in DMSO and added at varying concentrations (0.5 to 10 μM) to the solution of tubulin before polymerization. The results are expressed as percentage inhibition of polymerization relative to the controls.

The $IC_{50}$ is defined as the concentration of product which inhibits by 50% the rate of polymerization of tubulin.

Measurement of the Inhibition of the Polymerization of Tubulin as a Function of the Compounds of Formula (I)

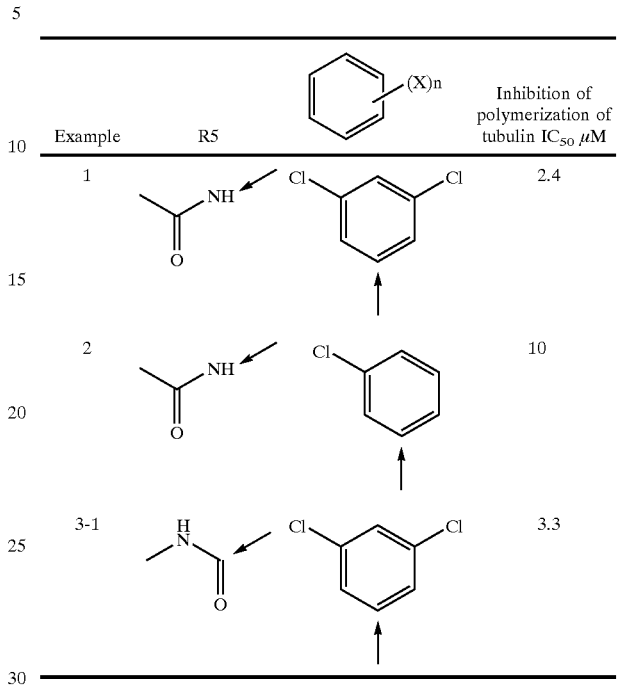

A product whose $IC_{50}$ is less than or equal to 3 μM is considered to be very active. Of the three compounds tested, those bearing two chlorine residues appear to be more active.

EXAMPLE 5

Evaluation of the Inhibition of Proliferation of HeLa Cells

The proliferation of HeLa cells is evaluated by measuring the incorporation of [$^{14}C$]thymidine in the following manner. The HeLa cells (tumour epithelial cells of human origin) are cultured in a DMEM medium (Gibco) which contains 10% of heat-inactivated foetal calf serum and antibiotics (1% penicillin, 1% streptomycin). To carry out the proliferation test, the cells are inoculated into 96-well Cytostar microplates (Amersham), at the rate of 5000 cells per well. [$^{14}C$]Thymidine (0.1 μCi/well) is then added and the compounds to be evaluated are added at concentrations varying up to 10 μM; the DMSO used to solubilize the compounds should not exceed 0.5% in the medium. 48 hours after incubation at 37° C., the radioactivity incorporated into the cells is measured by counting the plate in a TRI-LUX counter (Wallac). The results are expressed as % counts incorporated into the cells in the presence of compounds as compared with the control for proliferation.

The $IC_{50}$ is defined as the concentration of product which reduces by 50% the radioactivity compared with an untreated control.

Measurement of the Inhibition of Proliferation of HeLa Cells in the Presence of Compounds of Formula (I)

| Example | R5 | n | Inhibition of proliferation of HeLa cells IC$_{50}$ μM |
|---|---|---|---|
| 1 | —NH—C(=O)—CH₃ | 3,5-dichlorophenyl | 0.05 |
| 2 | —NH—C(=O)—CH₃ | 3-chlorophenyl | 2.3 |

It is considered that a product whose IC$_{50}$ is less than 1 μM is cytotoxic.

Among the two compounds tested, compound 1 exhibits advantageous characteristics as regards the inhibition of cell proliferation.

EXAMPLE 6

Evaluation of the Effect of Detachment of Endothelial Cells HDMEC

The evaluation of the detachment of the endothelial cells in vitro is determined in the following manner. The HDMEC (Human Dermal Microvascular Endothelial Cells, Promocell, c-122102) cells are cultured in an ECGM-MV medium which contains 5% heat-inactivated foetal calf serum, growth factors (EGF 10 ng/ml, hydrocortisone 1 μg/ml, 0.4% growth factor with heparin) and antibiotics (amphotericin 50 ng/ml and gentamicin 50 μg/ml). For the detachment test, the HDMECs are inoculated at 5000 cells per well into clear-bottom 96-well plates (Costar) preadsorbed with fibronectin (10 μg/ml) or vitronectin (1 μg/ml) or gelatin. Twenty-four hours later, the culture medium is replaced with the medium ECGM-MV 0.1% BSA (bovine serum albumin) containing the products indicated. The concentrations tested are 0.1–0.3 and 1 μM for each product. After two hours of treatment, the cells are labelled for one hour with calcein (1.6 μg/ml, Molecular Probes) in ECGM-MV 0.1% BSA medium. The detached cells are then removed by washing with ECGM-MV 0.1% BSA medium; 100 μl of medium is added to each well. The fluorescence of the cells which remain attached to the substratum of the wells is counted with the aid of a fluorimeter, Spectrafluor Plus (Tecan, excitation 485 nm, and emission 535 nm). The data are the mean of six different samples and are expressed as a percentage of the control (untreated cells).

| Example | R5 | 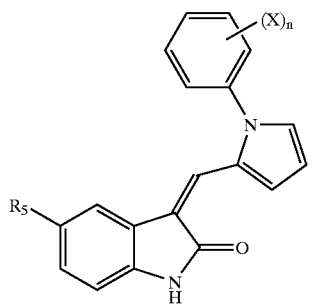 | Percentage detachment of the HDMEC cells induced by 1 μM of compound |
|---|---|---|---|
| 1 | —NH—C(=O)—CH₃ | 3,5-dichlorophenyl | 29% |

A cell detachment effect greater than or equal to 15% is considered as significant. Product 1 therefore has, in addition to properties of inhibition of tubulin and of inhibition of the cell proliferation of the HeLa cells tested, a marked action on the detachment of endothelial cells.

What is claimed is:

1. A compound of formula (I)

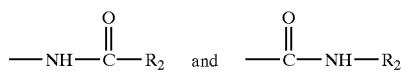

wherein:

R$_5$ is selected from the group consisting of:

$$—NH—\overset{O}{\underset{\|}{C}}—R_2 \quad \text{and} \quad —\overset{O}{\underset{\|}{C}}—NH—R_2$$

R$_2$ is C$_1$–C$_3$ alkyl;

X is Cl, Br, or F; and n is forms 1 and 3, in the E or Z form, or a mixture of the two stereoisomeric 2. The compound according to claim 1, wherein R$_2$ is a methyl group.

3. The compound according to claim 1, wherein X is Cl.

4. The compound according to claim 1, wherein n is equal to 2.

5. The compound according to claim 1, selected from the group consisting of:

3[N-(3,5-dichlorophenyl)pyrrol-2-yl]-5-acetylaminoindolin-2-one

3-[N-(3-chlorophenyl)pyrrol2-yl]-5-acetylaminoindolin-2-one, and

3-[N-(3,5-dichlorophenyl)pyrrol-2-yl]indolin-2-one-5-yl-N-methylcarboxamide.

6. A process of preparing a compound according to claim 1 comprising reacting a compound of formula (II)

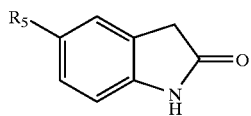

wherein R$_5$ is defined as for formula (I) in claim 1, with a compound of formula (III)

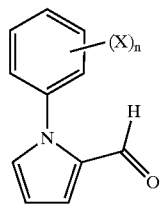

wherein X and n are as defined for formula (I) in claim 1, in the presence of a catalytic quantity of organic base and a protic solvent at a reaction temperature from about 20° to reflux temperature of the protic solvent.

7. The process according to claim 6, wherein said organic base is piperidine.

8. The process according to claim 6 wherein said protic solvent is ethanol.

9. The process according to claim 6 wherein said reaction temperature is the reflux temperature of the protic solvent.

10. A pharmaceutical composition, comprising a compound of claim 1 or a pharmacologically tolerable salt thereof and one or more physiologically acceptable excipients.

* * * * *